United States Patent
Simonsen et al.

(10) Patent No.: US 9,943,251 B2
(45) Date of Patent: Apr. 17, 2018

(54) STRETCH SENSOR DEVICE

(75) Inventors: Ole Simonsen, Vrå (DK); Henrik Karstoft, Højbjerg (DK); Simon Lind Kappel, Aarhus N (DK); Dan Hermann, Kgs. Lyngby (DK); Michael Skovdal Rathleff, Aalborg (DK); Peter Ahrendt, Tranbjerg (DK)

(73) Assignees: Region Nordjylland, Aalborg Ø (DK); Ingeniørhøjskolen Aarhus Universitet, Aarhus C. (DK)

( * ) Notice: Subject to any disclaimer, the term of this patent is extended or adjusted under 35 U.S.C. 154(b) by 574 days.

(21) Appl. No.: 14/346,414

(22) PCT Filed: Sep. 11, 2012

(86) PCT No.: PCT/DK2012/050341
§ 371 (c)(1),
(2), (4) Date: Jun. 18, 2014

(87) PCT Pub. No.: WO2013/041101
PCT Pub. Date: Mar. 28, 2013

(65) Prior Publication Data
US 2014/0336538 A1   Nov. 13, 2014

(30) Foreign Application Priority Data
Sep. 22, 2011   (DK) .................. 2011 70521

(51) Int. Cl.
*A61B 5/103* (2006.01)
*A61B 5/117* (2016.01)
(Continued)

(52) U.S. Cl.
CPC ............ *A61B 5/112* (2013.01); *A61B 5/1126* (2013.01); *A61B 5/6829* (2013.01); *A61B 5/1038* (2013.01);
(Continued)

(58) Field of Classification Search
CPC ..... A61B 5/1038; A61B 5/1116; A61B 5/112; A61B 5/6807; A61B 5/6829
See application file for complete search history.

(56) References Cited

U.S. PATENT DOCUMENTS 6,360,597 B1   3/2002   Hubbard, Jr.
6,493,652 B1   12/2002   Ohlenbusch et al.
(Continued)

FOREIGN PATENT DOCUMENTS

EP   1212800 B1   12/2007
WO   9918480 A1   4/1999

OTHER PUBLICATIONS

Bandholm, Thomas, MSc, et al., "Foot Medial Longitudinal-Arch Deformation During Quiet Standing and Gait in Subjects with Medial Tibial Stress Syndrome," The Journal of Foot & Ankle Surgery, vol. 47, No. 2, Mar./Apr. 2008, pp. 89-95.
(Continued)

*Primary Examiner* — Devin Henson
(74) *Attorney, Agent, or Firm* — Woodard, Emhardt, Moriatry, McNett & Henry LLP

(57) ABSTRACT

The invention relates to a method for determining stretch values and movement of body parts, e.g. a foot, by analyzing stretch data from a stretch sensor. By analyzing data from the stretch sensor it is possible to determine stretch samples which are associated with particular motion phases. Thereby the stretch values determined from the stretch samples have a particular physical meaning since they are associated with particular motion phases.

20 Claims, 4 Drawing Sheets

(51) Int. Cl.
*A61B 5/11* (2006.01)
*A61B 5/00* (2006.01)

(52) U.S. Cl.
CPC .......... *A61B 5/1116* (2013.01); *A61B 5/6807* (2013.01); *A61B 5/6833* (2013.01)

(56) References Cited

U.S. PATENT DOCUMENTS

| | | |
|---|---|---|
| 6,809,462 B2 | 10/2004 | Pelrine et al. |
| 2008/0082025 A1 | 4/2008 | Hughes et al. |
| 2009/0165190 A1 | 7/2009 | Araki et al. |
| 2010/0324457 A1* | 12/2010 | Bean ............... A61B 5/4519 600/595 |
| 2012/0035509 A1* | 2/2012 | Wilson ............ A61B 5/1038 600/592 |
| 2012/0255160 A1* | 10/2012 | Boone ............. A61B 5/1038 29/592 |
| 2013/0006583 A1* | 1/2013 | Weast ............... A61B 5/112 702/189 |

OTHER PUBLICATIONS

Omasta, Milan, et al., "Finite Element Analysis for the Evaluation of the Structural Behaviour of a Prosthesis for Trans-Tibial Amputees," Medical Engineering & Physics 34, 2012, pp. 38-45.

Preece, Stephen J., et al., "Automatic Identification of Gait Events Using an Instrumented Sock," Journal of NeuroEngineering and Rehabilitation 2011, 8:32, 10 pages.

PCT International Search Report for PCT International Patent Application No. PCT/DK2012/050341, dated Dec. 11, 2012.

* cited by examiner

STRETCH SENSOR DEVICE

FIELD OF THE INVENTION

The invention relates to a method for determining movement of a human or animal body part on basis of measured stretch data.

BACKGROUND OF THE INVENTION

A non-optimal movement pattern of the body or parts of the body is a major cause of pain and lesions or injuries in the locomotion system. Movement analysis is crucial for prophylaxis, diagnosing and treatment of such lesions, and in sports an optimal movement pattern is essential for optimal and injury free performance.

Until now movement analysis has primarily been performed by monitoring movement of points on the body during motion, e.g. by use of advanced video technology where retro reflective optical markers on the body are tracked during motion with one or multiple video cameras. However, such video-based methods for analysing body motion and body loads are impractical since they normally require use of a treadmill and large dedicated rooms.

Accordingly, there is a need to enable monitoring of body motion without restricting the motion to be carried out in a particular environment, room or with use of a treadmill.

U.S. 2010324457 discloses a system that records position data for portions of a body as a function of time. The position data can be collected from one or more sensors secured to the body either individually or using a patch. The sensors, in some embodiments, can include stretch sensors that produce a change in electrical resistance as the stretch sensors are stretched as a result of body movement. A data logger can be used to record the data. Various other elements such as a feedback mechanism or a manual pain indicator can also be included.

The inventor of the present invention has appreciated that improved methods analysing body motion for determining body load is of benefit, and has in consequence devised the present invention.

SUMMARY OF THE INVENTION

It would be advantageous to achieve improved method for determining body loads during motion. It would also be desirable to enable determination of body loads without restricting the motion to be performed in a particular environment. In general, the invention preferably seeks to mitigate, alleviate or eliminate one or more of the above mentioned disadvantages singly or in any combination. In particular, it may be seen as an object of the present invention to provide a method that solves the above mentioned problems, or other problems, of the prior art.

To better address one or more of these concerns, in a first aspect of the invention a sensor device is presented that is configured to process stretch data from a stretch sensor for determining a stretch value of a body part, where the sensor device comprises a processor configured to analyse the stretch data to identify a portion of the stretch data which corresponds to a motion of the body part, where the portion of the stretch data is identified so that the portion contains first and second stretch data points associated with respective first and second motion-phases of the body part, analyse the identified portion of stretch data to determine first and second sensor values of the respective first and second stretch data points, determine a stretch value from the first and second sensor values.

It is understood that the first and second stretch data points are separated in time and located within a cyclic period of the stretch data.

Since the sensor device is configured to determine a stretch value from specific stretch data samples of the measured stretch data—where the specific stretch data samples are associated with specific motion phases—it is ascertained that the stretch value is indicative of a particular stretch directly related, e.g. to the navicular drop. The motion phases may be predefined phases such as particular motion phases of a foot.

The determination of stretch values may be used for determining movement of the body part, i.e. high stretch values which may indicate a high harmful overload. The sensor device may be used by professionals for determining load values of patients or the sensor device may be used by non-professionals e.g. by athletes for determining the load of a body part during training. For example, the sensor device may be used by runners for avoiding overloading of the foot by determining when the stretch values of the foot are becoming too high. Thereby, the athlete is able to maximize training efforts without the risk of overload injuries.

Herein the word movement is used to define the stretch or movement of a body part, i.e. a stretch or movement between two points on a body part, such as between the tuberosity of the navicular bone and the center of the medial malleolus. The movement may be used for assessing the load of the particular body part. The word motion is used to define e.g. walking, running or other motions of a body part.

The sensor device is particularly advantageous since it enables determination of stretch values by use of a single sensor. That is, no other sensors than a stretch sensor is required since the sensor device enables determination of stretch values in a way so that the stretch values are synchronized with the body motion.

In an embodiment of the invention the body part is a foot, where the portion of the stretch data corresponds to a walking or running motion, where the first motion-phase of the foot is the heel strike, and where the second motion-phase of the foot is the mid stance, i.e. the phase where both the toe and the heel are in contact with the ground.

In an embodiment the first data point is determined by determining a minimum value within at least a fraction of the identified portion of the stretch data and the second data point is determined by determining a maximum value within at least a fraction of the determined portion of the stretch data.

In an embodiment the second data point is determined by determining a maximum value within at least a fraction of the portion of the stretch data and the first data point is determined by determining a minimum value located in time before the second data point.

The stretch data may have a profile so that the maximum value always corresponds to a specific motion phase (e.g. both heel and toes are in contact with ground) and so that the minimum value located in the determined portion of the stretch data and before the maximum value always corresponds to another specific motions phase (heel impact).

In an embodiment of the processor comprised by the sensor device is further configured for determination of a period of time between the first and second stretch data points. This period may advantageously be used as a second measure (in addition to the first measure of stretch data) for determining the movement of the body part. E.g. a period of time between the first and second stretch data points which increases may indicate a decreased stability (corresponds to a softness) of the body part and, thereby, an increased risk of an overload injury.

In an embodiment the period of time between the first and second stretch data points is compared with a period of time of the cyclic walking motion for determination of the stability of the body part.

In an embodiment the sensor device further comprises a processor or filtering electronics for low pass filtering the stretch data.

A second aspect of the invention relates to a sensor system comprising
  a sensor device according to the first aspect,
  a stretch sensor configured to be directly or indirectly connected to a body part for determining a stretch value of a body part.

The stretch sensor may be a capacitive or resistive sensor which changes its capacitance or resistance as a function of elongation. Accordingly, stretch data can be determined from the stretch sensor by monitoring changes in the sensor's electrical characteristics.

A third aspect of the invention relates to a method for determining a stretch value of a body part, the method comprises,
  obtaining stretch data from a stretch sensor connected to the body part,
  analysing the stretch data to identify a portion of the stretch data which corresponds to a motion of the body part, where the portion of the stretch data is identified so that the portion contains first and second stretch data points associated with respective first and second motion-phases of the body part,
  analysing the identified portion of stretch data to determine first and second sensor values of the respective first and second stretch data points,
  determining a stretch value from the first and second sensor values.

A fourth aspect of the invention relates to a computer program containing computer program instructions for enabling processor to carrying out of a method according to the third aspect.

In summary the invention relates to a method for determining stretch values and loading of body parts, e.g. a foot, by analysing stretch data from a stretch sensor. By analysing the stretch sensor it is possible to determine stretch samples which are associated with particular motion phases. Thereby the stretch values determined from the stretch samples have a particular physical meaning since they are associated with particular motion phases.

In general the various aspects of the invention may be combined and coupled in any way possible within the scope of the invention. These and other aspects, features and/or advantages of the invention will be apparent from and elucidated with reference to the embodiments described hereinafter.

BRIEF DESCRIPTION OF THE DRAWINGS

Embodiments of the invention will be described, by way of example only, with reference to the drawings, in which.

DETAILED DESCRIPTION OF EMBODIMENTS

Figure 1:
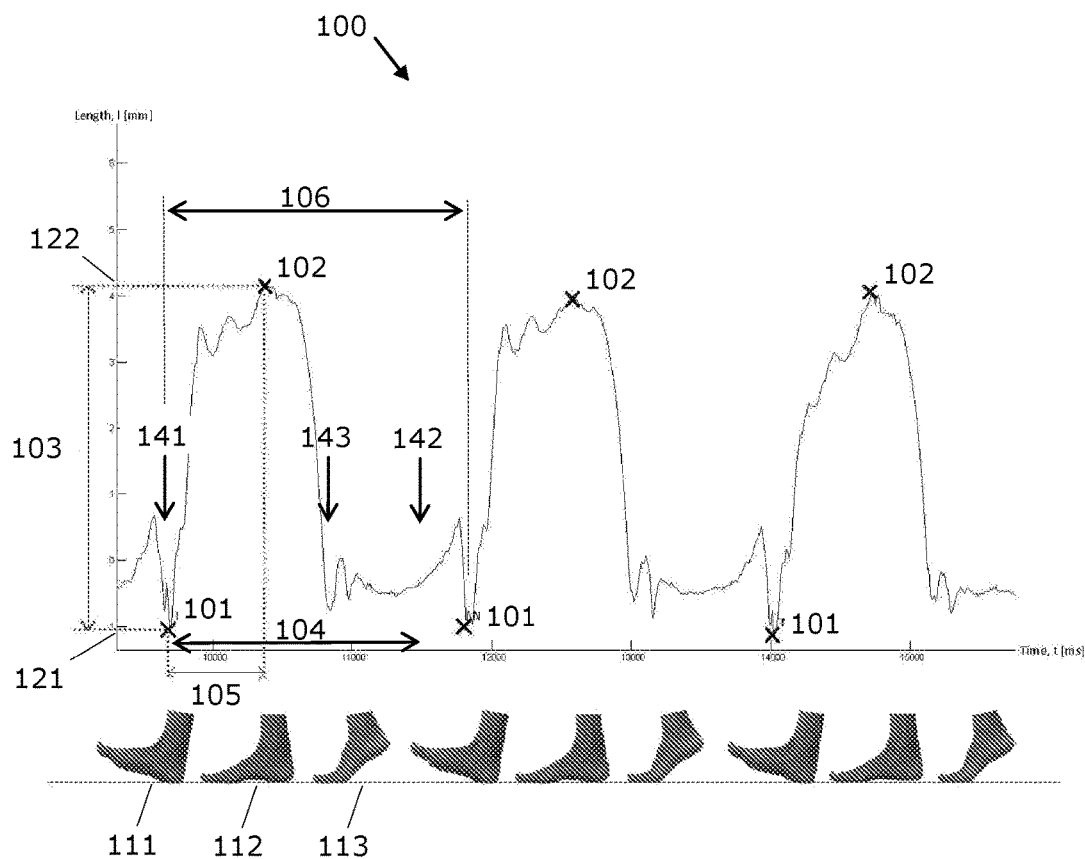
FIG. 1 shows a curve 100 of measured stretch data.

FIG. 1 shows a stretch data curve 100 of measured stretch data from a stretch sensor. The stretch data curve 100 is analyzed by a sensor device for determining a stretch value 103 of e.g. a foot.

Figure 2:
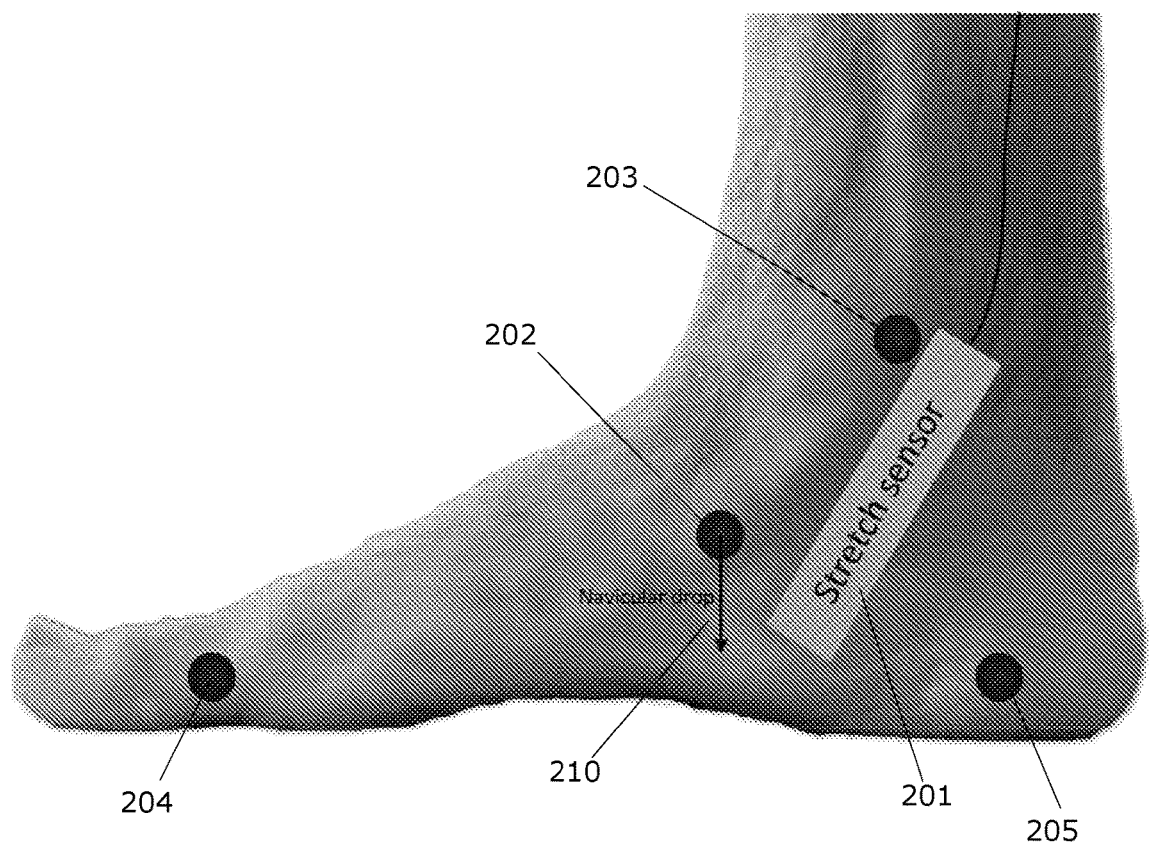
FIG. 2 shows a stretch sensor 201 attached to a foot for determining a stretch of the foot such as navicular drop.

FIG. 2 shows a stretch sensor 201 attached to a foot for measuring a stretch of the foot. In FIG. 2 the sensor is located close to the points 202 (the tuberosity of the navicular bone), and 203 (the center of the medial malleolus) for measuring the navicular drop 210 of the point 202. The heel part 205 and the toe part 204 of the foot are also indicated. A stretch of the foot such as the navicular drop 210 is indicative for the load of the foot.

From the stretch data curve 100 in FIG. 1 it is possible to determine stretch values of the foot. However, in order to relate the measured stretch to e.g. load of the foot the measured stretch has to be associated with a particular motion of the foot. By identifying particular motion phases of the foot the stretch values measured when the foot is in these phases can be used to quantify the load of the foot. An example of determining a stretch for a particular motion of the foot is given below.

The motion of the foot is shown in FIG. 1 with three motion phases 111-113. The first motion phase 111 is the heel strike where the heel 205 contacts the ground, the second motion phase 112 is the mid stance, i.e. the phase where both the toe 204 and the heel 205 contacts the ground and the third phase 113 is the toe-off, i.e. the phase where only the toe 204 contacts the ground before set-off.

In the second phase 112 the stretch between the first and second points 202,203 are maximal, and in the first phase 111 the stretch between the first and second points 202,203 are minimal. Accordingly, the difference between the stretch values in the first and second phases 111, 112 gives a measure of the loading of the foot during walking or running.

In FIG. 1 the measured stretch value or sensor value 121 at the first stretch data point 101 corresponding to the first motion phase 111, is a global minimal value during the entire data curve 100 or at least during a motion period 106. Similarly, the sensor value 122 at the second stretch data point 102 corresponding to the second motion phase 112, is a global maximal value during the entire data curve 100 or at least during a motion period 106. Accordingly, in an embodiment the first and second stretch data points 101, 102 could simply be determined by determining the minimal and maximal sensor values 121,122 in a given time interval of the data curve 100. However, since it may be important that the determined stretch data points are associated with particular predetermined motion phases, this simple approach could lead to an incorrect stretch value 103 if e.g. the minimum value of some reason is not located at the first motion phase 111, but at some other motion phase 143.

Figure 4:
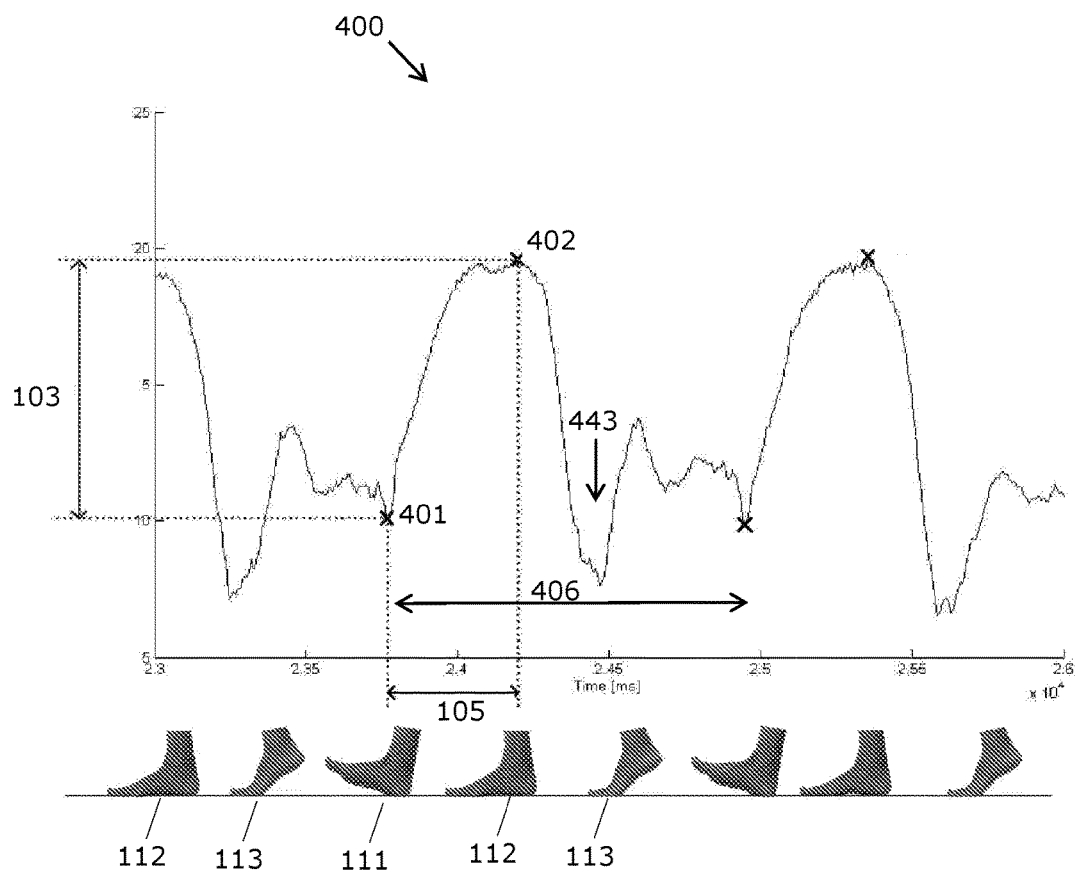
FIG. 4 shows a second example of a curve 400 of measured stretch data.

As an example, FIG. 4 shows a stretch data curve 400 of measured stretch data from a stretch sensor. In FIG. 4 the sensor value of the first stretch data point 401 corresponding to the first motion phase 111, is not a minimal value within a motion period 406. Only the sensor value at the second stretch data point 402 corresponding to the second motion phase 112 is a maximal value during a motion period. The minimum value is located at some other motion phase 443.

Accordingly, FIG. 4 shows an example where the first stretch point 401 cannot be determined by the simple approach where the first stretch point 401 is assumed to be a minimum value during a motion period.

To avoid incorrectly determined stretch values, the stretch data 100 is advantageously analyzed to identify a portion 104 of the stretch data which corresponds to some motion cycle (e.g. the cycle comprising motion phases 111-113) of e.g. the foot, where data is analyzed in a way so that this portion 104 contains the first and second stretch data points 101,102 associated with the respective first and second motion-phases 111,112 of the foot.

The portion 104 may be identical to an entire period 106 or the portion may be a fraction of a complete period 106. Here a period is understood as a period of a harmonic signal, for example the cyclic data curve 100.

The portion 104 of the stretch data containing the first and second data points 101,102 may be identified from a correlation analysis of the stretch data to identify e.g. the high frequency dip of the curve 100 near the start point 141 of a period and the low frequency dip near the end point 142 so as to identify the illustrated fraction 104 of an entire period 106 of the cyclic motion pattern. Accordingly, the portion 104 of the stretch data 100 may be determined by determining a start point 141 and an end point 142 so that the stretch data contained between the start point 141 and the end point 142 corresponds to at least a fraction of one period 106 of a period of the motion.

Having identified the portion 104 of stretch data 100 the first and second sensor values 121, 122 of the respective first and second stretch data points 101,102 can be determined, and from the sensor values 121, 122 a resulting stretch value 103 can be determined, e.g. by determining the difference between the first and second sensor values 121, 122.

Having identified the portion 104 of the stretch data, the first data point 101 may be determined by determining a minimum value within at least a fraction of the identified portion, e.g. a first fraction including the start point of the portion 104 and having a given duration equal to a fraction of the duration of the entire portion 104. Similarly, the second data point 102 may be determined by determining a maximum value within at least a fraction of the determined portion 104 of the stretch data, e.g. a second fraction starting where first fraction ends and ending at the end point of the portion 104.

Assuming that the second data point 102 can be uniquely identified from the maximum value of the stretch data, then according to an embodiment the second data point 102 can be determined by determining a maximum value within at least a fraction of the portion 104 of the stretch data 100. Having initially identified the second data point, the first data point 101 can be determined by determining a minimum value located in time before the second data point 102 and within the portion 104.

From the above discussion it is clear that a period 106 or a fraction thereof, i.e. a portion 104, can be identified by analysing the stretch data signal e.g. by frequency analysis. It is also clear that the first and second data points 101, 102 corresponding to first and second motion phases 111, 112 can be identified by analysing the data within the identified period 106 or portion 104 thereof, e.g. by searching for minimal and maximal values, e.g. by use of a peak detector.

In an aspect of the invention a period of time 105 between the first and second stretch data points 101, 102 is determined e.g. by calculating the difference of the time stamps of the first and second stretch data points. The period of time 105 gives an indication of the softness of the foot or other body part and, thereby, an indication of the loading of the foot since the softness tends to increase with increased loading of the foot. Accordingly, the change of the period of time 105 during monitoring of stretch data 100 may be used for assessing the softness of the foot. A decrease in the time period corresponds to an increase in softness. The period of time 105 may be compared with the period of time 106 of the cyclic motion, or a fraction 104 thereof, to get an absolute measure of the softness of the body part such as the foot.

The sensor values from the stretch sensor may be noisy and, therefore, a processor or filtering electronics for low pass filtering the stretch data may be used.

Figure 3:
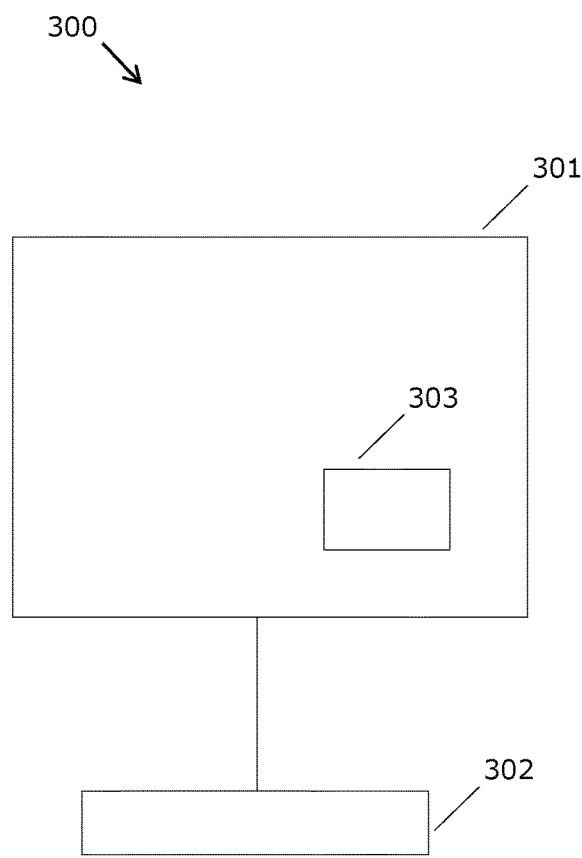
FIG. 3 shows sensor device 301 configured to process stretch data from a stretch sensor 302.

FIG. 3 shows a sensor system 300 which comprises the sensor device 301 for analysing stretch data and a stretch sensor 302. The sensor device 301 may include a processor 303 configured for analysing the stretch data and determining stretch values 103. The processor need not be part of the sensor device 301.

The sensor system 300 may be configured in various ways. The sensor device 301 may be an electronic device configured to be carried by the user, e.g. on a wrist. Such a sensor device may receive stretch data wirelessly from the stretch sensor which may include a transmitter for transmitting data to a receiver of the sensor device 301. The sensor device 301 may include a display for displaying results of determined stretch values. The sensor device may be configured so that only part of the processing of stretch data 100 is carried out by the sensor device 301 whereas other parts of the processing of stretch data may be carried out by other processing devices, e.g. a computer which is connectable to the sensor device 301. Accordingly, the sensor device 301 may contain a storage for storage of stretch data or processed stretch data, so that another processor unit may be connected (wirelessly or wired) to the sensor device. The stretch sensor 302 may also contain a processor and or a storage for storing measured stretch data 100 so that the sensor device 301 or some other processor may be connected to the stretch sensor 302 via a transmitter-receiver pair for further processing of the stored stretch data.

Whereas the determination of stretch values and analysis of stretch values has been described on basis of a foot and foot motion, the invention is equally applicable to other body parts and their motion phases. For example, the stretch sensor may be attached to the shoulder of a person in order to determine stretch values of shoulder by identifying a portion 104 of the stretch data which corresponds to at least a fraction of a complete period of cyclic motion of the shoulder, where the portion of the stretch data is identified so that the portion contains first and second stretch data points 101, 102 associated with respective first and second motion-phases of the shoulder, and by analysing the identified portion of stretch data to determine first and second sensor values 121, 122 so that a stretch value 103 can be determined. The invention described herein may be particularly, but not exclusively, applicable to determining stretch values of body parts where a cyclic motion of the body part can be identified.

The stretch sensor 302 may be connected to a body part by connecting the sensor directly to the skin (e.g. by use of some adhesive material), or the sensor may be indirectly attached, e.g. by integrating the sensor with a sock or a shoe.

An aspect of the invention include socks, shoes or bandages wherein the sensor system or the stretch sensor is integrated for enabling indirect attachment of the sensor.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A method for determining stretch values of a body part, wherein the body part includes first and second points that move relative to each other when the body part moves, the method comprising:
   connecting a stretch sensor to the body part near both the first and second points such that movement of the first point relative to the second point changes the elongation of the stretch sensor, wherein the stretch sensor is a capacitive or resistive sensor, which changes its capacitance or resistance as a function of elongation;
   while moving the body part, at a processor associated with the stretch sensor, obtaining stretch data from the stretch sensor;
   processing, by the processor, the stretch data obtained from the stretch sensor with a sensor device to determine a stretch value of the body part, wherein the processor is configured to perform the method by:
      analysing the stretch data as cyclic stretch data while the body part is in motion;
      analysing the stretch data to identify portions of the cyclic stretch data which correspond to motions of the body part, wherein the portions of the stretch data are identified so that the portions contain first and second stretch data points associated with respective first and second motion-phases of the body part;
      analysing the cyclic stretch data to identify first and second stretch values by determining minimum and maximum sensor values;
      further analysing the cyclic stretch data confirming that the portions contain an entire period of a cyclic harmonic signal containing first and second stretch data points associated with the respective first and second motion-phases of the body part and distinguishing values related to other motion phases including excluding sensor values that occur in a third motion-phase from being identified as the minimum sensor value;
      analysing the identified portions of cyclic stretch data to determine first and second sensor values of the respective first and second stretch data points;
      calculating stretch values by determining at least the difference between the first and second sensor values associated respectively with the first and second motion-phases; and
   transmitting the calculated stretch values to a receiver associated with the processor.

2. The method according to claim 1, wherein the body part is a foot, the identified portion of the cyclic stretch data corresponds to a walking or running motion, the first motion-phase of the foot corresponds to a heel strike, and the second motion-phase of the foot corresponds to where both a toe and the heel contacts the ground.

3. The method according to claim 1, wherein the first stretch data point is determined by determining a minimum value within at least a fraction of an identified portion of the stretch data and the second stretch data point is determined by determining a maximum value within at least a fraction of said identified portion of the stretch data.

4. The method according to claim 1, wherein the second stretch data point is determined by determining a maximum value within at least a fraction of a portion of the stretch data and the first stretch data point is determined by determining a minimum value located in time before the second stretch data point.

5. The method according to claim 1, further comprising determining a period of time between the first and second stretch data points within a portion of the stretch data.

6. The method according to claim 5, wherein the period of time between the first and second stretch data points is compared with a period of time of a cyclic walking motion for determining a softness of the body part.

7. The method according to claim 1, wherein the processor or separate filtering electronics is used for low pass filtering the stretch data.

8. A computer program containing computer program instructions for enabling the processor to carry out the method according to claim 1.

9. The method according to claim 1, further comprising assessing the load of the body part by monitoring the determined stretch values.

10. The method according to claim 1, wherein the body part is a joint.

11. A sensor system for determining stretch values of a body part that includes first and second points that move relative to each other when the body part moves, the system comprising:
   a stretch sensor configured to be directly connected to the body part near both the first and second points such that movement of the first point relative to the second point changes the elongation of the stretch sensor;
   a sensor device comprising a processor and in communication with the stretch sensor, the sensor device configured for:
      obtaining stretch data from the stretch sensor, wherein the stretch sensor is a capacitive or resistive sensor, which changes its capacitance or resistance as a function of elongation;
      wherein the sensor device is configured to process stretch data from stretch sensor for determining a stretch value of the body part and wherein the processor is configured for:
         analysing the stretch data while the body part is in motion;
         analysing the stretch data to identify portions of the stretch data which correspond to motions of the body part wherein the portions of the stretch data are identified so that the portions contain first and second stretch data points associated with respective first and second motion-phases of the body part;
         analysing the cyclic stretch data to identify first and second stretch values by determining minimum and maximum sensor values;

further analysing the cyclic stretch data to confirm that the portions contain an entire period of a cyclic harmonic signal containing first and second stretch data points associated with the respective first and second motion-phases of the body part and to eliminate values related to other motion phases including excluding sensor values that occur in a third motion-phase from being identified as the minimum sensor value;

analysing the identified portions of stretch data to determine first and second sensor values of the respective first and second stretch data points;

calculating stretch values by determining at least the difference between the first and second sensor values associated respectively with the first and second motion-phases; and transmitting the calculated stretch values to a receiver associated with the processor.

12. The sensor system according to claim 11, wherein the body part is a foot, the portion of the stretch data corresponds to a walking or running motion, the first motion-phase of the foot corresponds to a heel strike, and the second motion-phase of the foot corresponds to where both a toe and the heel contacts the ground.

13. The sensor system according to claim 11, wherein the first stretch data point is determined by determining a minimum value within at least a fraction of an identified portion of the stretch data and the second stretch data point is determined by determining a maximum value within at least a fraction of said identified portion of the stretch data.

14. The sensor system according to claim 11, wherein the second stretch data point is determined by determining a maximum value within at least a fraction of a portion of the stretch data and the first stretch data point is determined by determining a minimum value located in time before the second stretch data point.

15. The sensor system according to claim 11, wherein the sensor device is configured to determine a period of time between the first and second stretch data points within a portion of the stretch data.

16. The sensor system according to claim 15, wherein the sensor device is configured to compare the period of time between the first and second stretch data points with a period of time of a cyclic walking motion to determine a softness of the body part.

17. The sensor system according to claim 11, wherein the processor or separate filtering electronics is used for low pass filtering the stretch data.

18. A method for determining stretch values of a foot during a walking or running motion, the method comprising:

obtaining, at a processor associated with a stretch sensor, stretch data from the stretch sensor directly connected to the foot, wherein the stretch sensor is a capacitive or resistive sensor that changes its capacitance or resistance as a function of elongation;

processing, by the processor, stretch data obtained from the stretch sensor with a sensor device to determine a stretch value of the foot, the sensor device comprises the processor which is configured to:

analyze the stretch data while the foot is in motion to identify portions of the stretch data that correspond to motions of the body part, wherein the portions of the stretch data contain first and second stretch data points associated with respective first and second motion-phases of the foot, wherein the first motion-phase of the foot corresponds to a heel strike, and the second motion-phase of the foot corresponds to where both a toe and the heel contacts the ground;

confirm that the portions of the stretch data contain portions of an entire period of a cyclic harmonic signal containing first and second stretch data points associated with the respective first and second motion-phases of the foot and to distinguish values related to other motion phases;

determine first and second sensor values of the respective first and second stretch data points by at least one of determining minimum and maximum sensor values, wherein the minimum sensor value is the minimum sensor value in the first motion-phase and the maximum sensor value is the maximum sensor value in the second motion-phase and determining a difference between the first and second sensor values;

calculating stretch values of the foot based at least in part on determining the difference between the first and second sensor values; and transmitting the calculated stretch values to a receiver associated with the processor.

19. The method according to claim 18, further comprising determining a period of time between the first and second stretch data points within a portion of the stretch data.

20. The method according to claim 18, wherein sensor values that occur in a third motion-phase are excluded from being identified as the minimum sensor value.

* * * * *

UNITED STATES PATENT AND TRADEMARK OFFICE
CERTIFICATE OF CORRECTION

| | |
|---|---|
| PATENT NO. | : 9,943,251 B2 |
| APPLICATION NO. | : 14/346414 |
| DATED | : April 17, 2018 |
| INVENTOR(S) | : Ole Simonsen |

It is certified that error appears in the above-identified patent and that said Letters Patent is hereby corrected as shown below:

On the Title Page

Assignee, please replace "Region Nordjylland" with --Region Nordjylland, Aalborg Sygehus--

Signed and Sealed this
Twenty-ninth Day of May, 2018

Andrei Iancu
*Director of the United States Patent and Trademark Office*